(12) United States Patent
Arcand et al.

(10) Patent No.: US 9,987,115 B2
(45) Date of Patent: Jun. 5, 2018

(54) FILM ENCAPSULATED PELVIC IMPLANT SYSTEM AND METHOD

(75) Inventors: Benjamin Y. Arcand, Minnetonka, MN (US); James A. Kazmierkoski, Minnetonka, MN (US); Dean W. Hacker, Minnetonka, MN (US); Emily R. Rolfes Meyering, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 432 days.

(21) Appl. No.: 14/007,646

(22) PCT Filed: Mar. 30, 2012

(86) PCT No.: PCT/US2012/031577
§ 371 (c)(1),
(2), (4) Date: Nov. 15, 2013

(87) PCT Pub. No.: WO2012/135699
PCT Pub. Date: Oct. 4, 2012

(65) Prior Publication Data
US 2014/0088343 A1 Mar. 27, 2014

Related U.S. Application Data

(60) Provisional application No. 61/469,499, filed on Mar. 30, 2011.

(51) Int. Cl.
*A61F 2/00* (2006.01)
*A61B 17/04* (2006.01)
(Continued)

(52) U.S. Cl.
CPC ........ *A61F 2/0063* (2013.01); *A61B 17/0401* (2013.01); *A61F 2/0045* (2013.01);
(Continued)

(58) Field of Classification Search
CPC .......... A61L 27/16; A61L 27/34; A61L 27/56; A61L 31/048; A61L 31/10; A61L 31/146;
(Continued)

(56) References Cited

U.S. PATENT DOCUMENTS 6,500,777 B1 * 12/2002 Wiseman ................. A61K 9/70
156/281
6,612,977 B2 9/2003 Staskin et al.
(Continued)

FOREIGN PATENT DOCUMENTS

EP 0815879 A2 1/1998
EP 0815879 * 1/2001
(Continued)

OTHER PUBLICATIONS

International Search Report and Written Opinion rendered by the International Searching Authority dated Jul. 24, 2012 for PCT Application No. PCT/US12/31577, 9 Pages.

*Primary Examiner* — Navin Natnithithadha
*Assistant Examiner* — Sunita Reddy
(74) *Attorney, Agent, or Firm* — Brake Hughes Bellermann LLP (57) ABSTRACT

Various embodiments of an implant devices and systems are provided. The implant devices can include a mesh or implant encapsulated or otherwise coated, in whole or in part, with a film or coating. The coating or film can include methylcellulose or ethylcellulose to provide tissue regeneration as a hydrogel, while also providing a stiff polymer film when dry.

20 Claims, 6 Drawing Sheets (51) Int. Cl.
*A61L 27/16* (2006.01)
*A61L 27/34* (2006.01)
*A61L 27/56* (2006.01)
*A61L 31/04* (2006.01)
*A61L 31/10* (2006.01)
*A61L 31/14* (2006.01)
*A61B 17/00* (2006.01)

(52) U.S. Cl.
CPC ............ *A61L 27/16* (2013.01); *A61L 27/34* (2013.01); *A61L 27/56* (2013.01); *A61L 31/048* (2013.01); *A61L 31/10* (2013.01); *A61L 31/146* (2013.01); *A61B 2017/00805* (2013.01); *A61B 2017/0427* (2013.01); *A61F 2210/0076* (2013.01)

(58) Field of Classification Search
CPC .......... C08L 1/28; C08L 23/12; A61F 2/0045; A61B 17/0401
USPC ................. 600/29–32, 37; 128/834, 885
See application file for complete search history.

(56) References Cited

U.S. PATENT DOCUMENTS

| | | | |
|---|---|---|---|
| 6,648,921 B2 | 11/2003 | Anderson et al. | |
| 6,691,711 B2 | 2/2004 | Raz et al. | |
| 7,025,063 B2 | 4/2006 | Snitkin et al. | |
| 7,303,525 B2 | 12/2007 | Watschke et al. | |
| 7,347,812 B2 | 3/2008 | Mellier | |
| 7,351,197 B2 | 4/2008 | Montpetit et al. | |
| 7,407,480 B2 | 8/2008 | Anderson et al. | |
| 7,500,945 B2 | 3/2009 | Cox et al. | |
| 2002/0147382 A1 | 10/2002 | Neisz et al. | |
| 2002/0151762 A1 | 10/2002 | Rocheleau et al. | |
| 2003/0009181 A1* | 1/2003 | Gellman | A61B 17/00234 606/151 |
| 2004/0151774 A1* | 8/2004 | Pauletti | A61K 9/0034 424/486 |
| 2006/0188546 A1* | 8/2006 | Giroux | A61L 27/34 424/426 |
| 2008/0113001 A1* | 5/2008 | Herweck | A61L 31/14 424/426 |
| 2008/0196729 A1* | 8/2008 | Browning | A61F 2/0045 128/834 |
| 2009/0005867 A1* | 1/2009 | Lefranc | A61F 2/0045 623/11.11 |
| 2009/0240104 A1* | 9/2009 | Ogdahl | A61B 17/0401 600/37 |
| 2009/0318843 A1* | 12/2009 | Van Holten | A61L 31/10 602/52 |
| 2010/0105979 A1 | 4/2010 | Hamel et al. | |
| 2011/0144417 A1 | 6/2011 | Jagger et al. | |
| 2012/0022321 A1 | 1/2012 | Dinh et al. | |

FOREIGN PATENT DOCUMENTS

| | | |
|---|---|---|
| WO | 2007097994 A2 | 8/2007 |
| WO | 2008057261 A2 | 5/2008 |

\* cited by examiner

FILM ENCAPSULATED PELVIC IMPLANT SYSTEM AND METHOD

PRIORITY

This application claims priority to and the benefit of U.S. Provisional Patent Application 61/469,499, filed Mar. 30, 2011, which is incorporated herein by reference in its entirety.

FIELD OF THE INVENTION

The present invention relates generally to surgical methods and apparatus and, more specifically, to a mesh or implant having a coating or film encapsulation to treat pelvic disorders, provide tissue fixation, facilitate tissue healing, and the like.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implantable mesh or implant that can be used to treat incontinence, and/or pelvic organ prolapse and other conditions.

SUMMARY OF THE INVENTION

The present invention describes pelvic mesh slings or implant devices and methods for treating pelvic conditions such as pelvic floor disorders, incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

The implant systems can include a mesh or implant encapsulated or otherwise coated, in whole or in part, with a film or coating. All or portions of the implant can be constructed of various acceptable polymer materials.

The coating or film can include methylcellulose or ethylcellulose to provide tissue regeneration as a hydrogel, while also providing a stiff polymer film when dry. The film can absorb moisture after implantation forming a hydrogel with relatively little stiffness.

The implant can be constructed of woven or knitted filament members to define a plurality of openings in the implant. Other embodiments of the implant can be constructed of a unitary or homogeneous sheet-like material formed via laser cutting, die cutting, stamping, and like procedures, to define a plurality of strut or like members to define the openings. The implant can include a support portion adapted to support selective tissue or other anatomical structures (e.g., bladder, bladder neck, urethra, pelvic floor, etc.). One or more tissue anchoring portions can be included to facilitate fixation of the implant upon implantation.

In certain embodiments, the encapsulation process provides a short-term alteration of mechanical properties of the mesh during the surgical implantation of the mesh and during the early in-growth period while it is being incorporated into the surrounding tissues. The material making up, in whole or in part, the coating or encapsulating film can be methylcellulose (or methylcellulose with altered functional groups) in certain embodiments. Methylcellulose is a hydrophilic polymer derived from plants which quickly forms a hydrogel in the presence of moisture (e.g., upon making contact with tissue and fluids after implantation). When fully dry, the methylcellulose forms a generally translucent flexible polymer coating on the implant. Other materials like or generally similar in formation or mechanical properties to methylcellulose can be employed as well as detailed further herein.

Embodiments of the present invention may be incorporated into or provided with various commercial products marketed by American Medical Systems of Minnetonka, Minn., such as the MiniArc®, Apogee®, Perigee®, Elevate® and like implant or pelvic disorder treatment solutions.

DETAILED DESCRIPTION OF PREFERRED EMBODIMENTS

Referring generally to FIGS. 1-19, various embodiments of implantable structures or mesh implant systems 10 and methods are shown. The implant systems 10 can include a mesh or implant 12 encapsulated or otherwise coated, in whole or in part, with a film or coating 13. All or portions of the implant 12 can be constructed of various acceptable materials, such as polypropylene, cellulose, polyvinyl, silicone, polytetrafluoroethylene, polygalactin, Silastic, carbonfiber, polyethylene, nylon, polyester (e.g., dacron), PLLA, PGA, and the like.

As further detailed herein, the coating or film 13 can include methylcellulose or ethylcellulose to provide tissue regeneration as a hydrogel, while also providing a stiff polymer film when dry. The film 13 can absorb moisture after implantation forming a hydrogel with relatively little stiffness.

Figure 1:
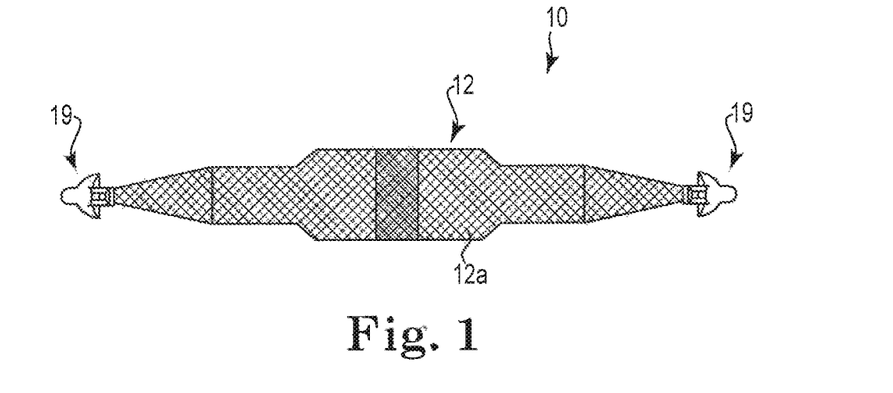
FIG. 1 depicts a generally elongate sling implant device in accordance with embodiments of the present invention.
Figure 2:
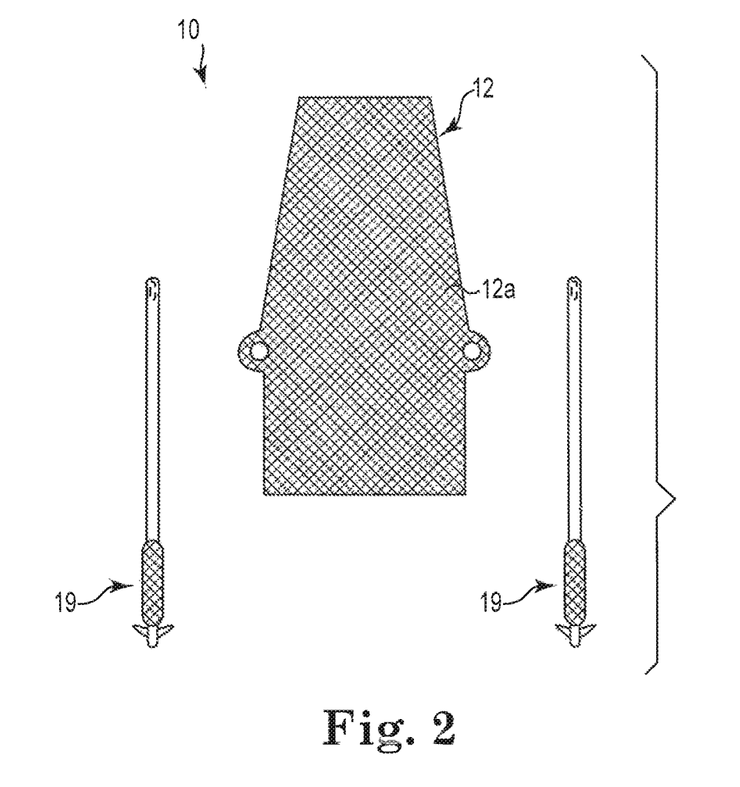
FIG. 2 depicts an implant system and device having separate support portions and anchoring portions in accordance with embodiments of the present invention.
Figure 3:
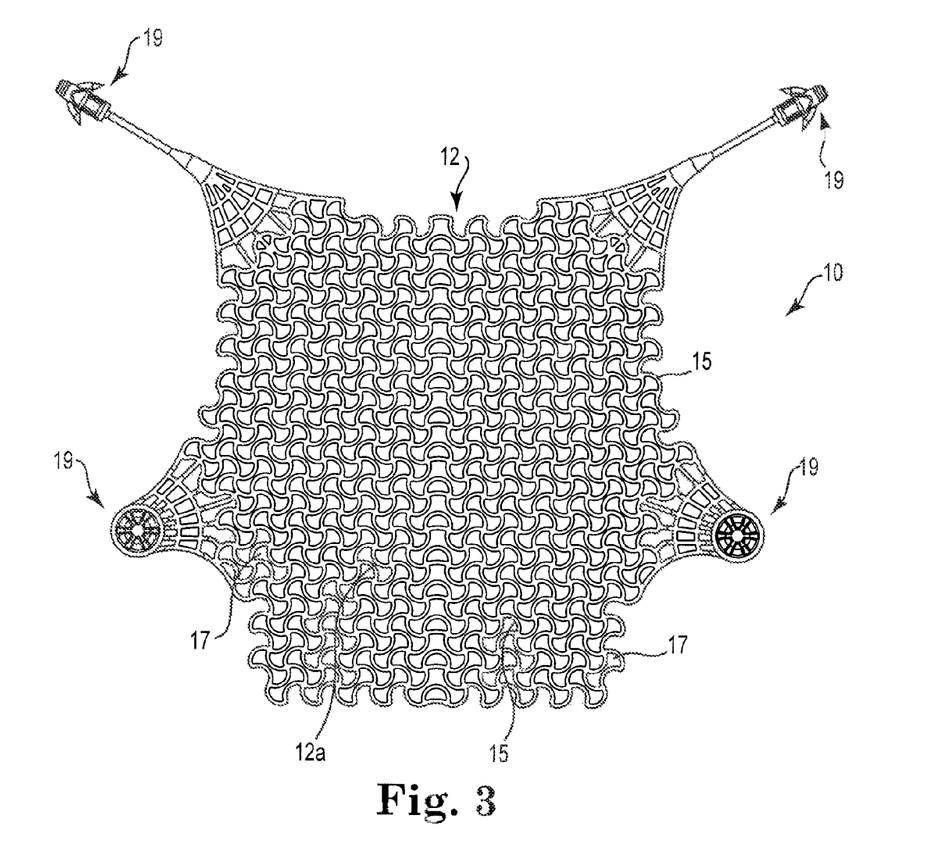
FIG. 3 depicts an implant device having a unitary support portion constructed of patterned strut members in accordance with embodiments of the present invention.

Exemplary embodiments of the implant 12 capable of including film 13 are shown in FIGS. 1-3. However, various other systems, implants, devices, features and methods detailed herein are envisioned for use with many, or can include, in whole or in part, known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2012/0022321, 2011/0144417, 2010/0105979, 2002/151762 and 2002/147382. Accordingly, the above-identified disclosures are fully incorporated herein by reference in their entirety.

The implant 12 can be constructed of woven or knitted filament members 15 to define a plurality of openings 17 in the implant 12. Other embodiments of the implant 12 can be constructed of a unitary or homogeneous sheet-like material formed via laser cutting, die cutting, stamping, and like procedures, to define a plurality of strut or like members 15 to define the openings 17. The implant 12 can include a support portion 12a adapted to support selective tissue or other anatomical structures (e.g., bladder, bladder neck, urethra, pelvic floor, etc.). One or more tissue anchoring portions 19 can be included to facilitate fixation of the implant 12 upon implantation.

Figure 4:
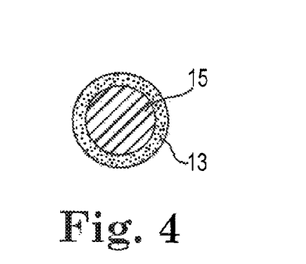
FIG. 4 depicts a partial cross-section view of a filament or strut member of an implant having a film or coating in accordance with embodiments of the present invention.

In certain embodiments, the encapsulation process provides a short-term alteration of mechanical properties of the mesh 12 during the surgical implantation of the mesh 12 and during the early in-growth period while it is being incorporated into the surrounding tissues. The material making up, in whole or in part, the coating or encapsulating film 13 can be methylcellulose (or methylcellulose with altered functional groups) in certain embodiments. Methylcellulose is a hydrophilic polymer derived from plants which quickly forms a hydrogel in the presence of moisture (e.g., upon making contact with tissue and fluids after implantation). A cross-sectional view of the film 13 applied to a filament or member 15 of embodiments of the implant 12 is shown in FIG. 4. When fully dry, the methylcellulose forms a generally translucent flexible polymer coating on the implant 12. Other materials like or generally similar in formation or mechanical properties to methylcellulose can be employed as well as detailed further herein.

Film encapsulated mesh 12 can address various perceived drawbacks relating to conventional mesh implants. The enhanced handling characteristics allows for much lighter meshes with a significant reduction in the overall construct of the implant 12. Further, scarring and tissue inflammation can be addressed with anti-inflammatory elution and by controlling the amount of in-growth into the mesh 12 in key anatomical locations.

Various features are enabled by encapsulating the mesh 12 in methylcellulose. First, the mesh 12 encapsulated in a film 13 of methylcellulose can improve the handling and placement of the mesh during the surgical procedure. Namely, it prevents the mesh from bunching and folding at the surgical site while providing some additional stiffness to the mesh 12 to help the surgeon position the mesh 12 into place. This film 13 can also provide a lighter mesh 12, with increased porosity to reduce infection and more closely match tissue properties. Moreover, the encapsulated mesh 12 can provide for very slender mesh patterns, and mesh patterns with multiple discrete portions that can be easily placed and positioned within the anatomy of the patient.

Figure 5:
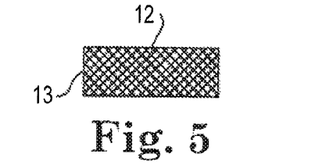
FIG. 5 depicts a portion of tensioned mesh or implant encapsulated within a film or coating in accordance with embodiments of the present invention.
Figure 6:
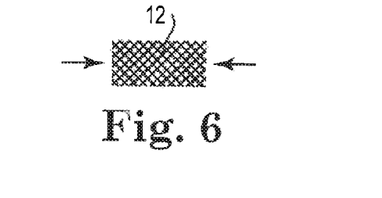
FIG. 6 depicts the portion of the mesh or implant of FIG. 5 after absorption or dissolution of the film or coating in accordance with embodiments of the present invention.
Figure 7:
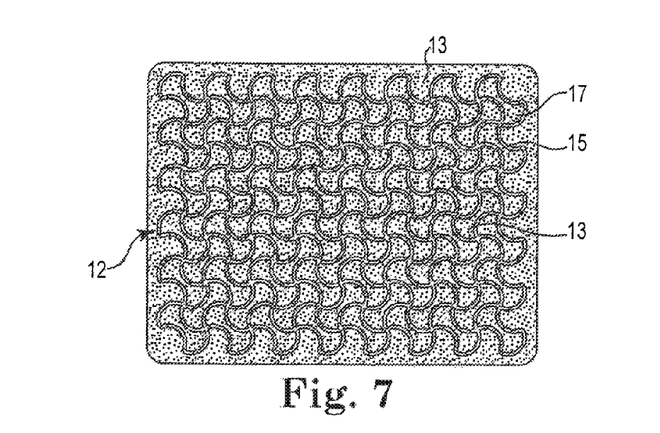
FIG. 7 depicts a portion of a mesh or implant fully encapsulated in a film or coating in accordance with embodiments of the present invention.

Another beneficial mechanical property achieved by applying the film 13 to the mesh 12 is the ability to lock or provide the mesh 12 in a tensioned configuration within the film 12 prior to deployment, as shown in FIGS. 5-6. This can permit certain mesh 12 constructs with a predetermined level of built-in tension that is releasable upon dissolution of the film 13 after implantation, e.g., over a period of time. The mesh 12 can be stretched or tensioned to a desired configuration, with the film or coating 13 provided at that point to maintain the mesh 12 in the tensioned state until dissolution of the film 13 (FIG. 5). Upon dissolution, when the material biodegrades or re-hydrates, original mesh mechanical properties or natural pre-tensioned state of the mesh 12 is restored within the patient (FIG. 6). The benefit of this would be to have a more controlled and repeatable sling or implant tension, thereby providing predictable results that are less affected by the implantation and deployment techniques of individual surgeons.

Additionally, the methylcellulose film 13 can be designed to improve the healing process. The film 13 forms a physical hydrogel barrier between tissues after surgery that prevents the adjacent tissues from adhering together. This property can be utilized in certain mesh 12 embodiments to control which portions of the implanted mesh 12 are designed to inhibit adhesion. This can reduce pain at sensitive tissue areas and assist in preventing shrinkage during scar tissue formation after implantation. In addition to the effect of the physical properties of the methylcellulose hydrogel in the healing process, the hydrogel is also a valid drug delivery platform—pharmaceuticals to control infection, inflammation and contribute to healing could be added to the film 13 construct and released upon implant and throughout the absorption period of the hydrogel.

The film 13 is employable with nearly all implantable mesh devices, including those formed of woven or knitted filaments, non-woven constructs, or unitary or homogeneous sheet-like implants formed via laser cutting, die cutting, stamping, and like procedures. Some of the benefits of a methylcellulose-coated mesh or implants 12 are provided in Table 1 below:

TABLE 1

Technical Benefits of Encapsulated Mesh or Implant

| | |
|---|---|
| Pre-tensioning | Prescribed tension built into the implant, no need for the surgeon to guess at the tension. |
| Handle-ability | A stiffer, more robust mesh resists bunching during implant. The film wets nicely to tissues, allowing the mesh to adhere to the surgical plane. |
| Diffuse Mesh | Ultra-light mesh can be designed and implanted that would not be practical to use without the support of the film. Delicate tissues and organs can be supported by equivalently delicate mesh. |
| Discrete Mesh | Multiple mesh captured in a single film can now be placed in one step. The mesh separates upon film dissolution and are free to move relative to each other, providing support only where needed. |
| Controlled in-growth | Thicker applications of film can prevent adhesion to the mesh. This could allow for less pain in highly flexible tissues. |
| Sleeve replacement | The film can replace sleeves or sheaths in certain devices and systems, reducing the procedural steps. |
| Drug elution | Methylcellulose is an ideal term pharmaceutical delivery method. |
| 3D shape formed mesh | Mesh can be preformed and locked into a 3D configuration for easier implantation. |

Methylcellulose is a chemical compound derived from cellulose. It is a hydrophilic white powder in pure form and dissolves in cold (but not in hot) water, forming a clear viscous solution or gel.

R = H or CH$_3$

Like cellulose, methylcellulose it is not digestible, not toxic, and not allergenic.

The chemical and physical properties of methylcellulose can be altered by substituting some of the hydroxyl groups or by refining the polymerization weight of the molecule. A substitute for medical applications can be carboxymethylcellulose. Methylcellulose is a biocompatible inert compound that cannot be metabolized by the body since human cells cannot synthesize cellulases to break down the molecule. However, in non-cross linked methylcellulose, the body is able to absorb the molecules and then excrete them at a later time.

Because the mesh implant 12, or a portion thereof, can be encapsulated in the film 13, discrete or very fine mesh portions can be provided. While thicker and easily handled during deployment, a finer mesh 12 is left after the film 13 is degraded or absorbed upon implantation. When the film 13 degrades, the individual mesh components 15 are freed from each other. Such a configuration has the advantage of prescribing mesh support to discrete locations and directions within the surgical space. This can hold an advantage for implant 12, such as vaginal implants, which need support in one direction, but minimal support in the orthogonal direction to allow for tissue stretching.

The methylcellulose prepared for certain embodiments of the present invention can utilize Colorcon Methocel pharmaceutical grade methylcellulose powder. In various embodiments, the hydrogel can be prepared by mixing 10 g of methylcellulose powder with 150 ml of water and stirred until dissolved. The solution can be degassed and spread onto the implant 12, or part of the implant 12, on a flat tray or wax paper for dipping or general application. The film 13 can be allowed to dry in air for approximately 24-48 hours or in an oven initially heated to around 250° F. and turned off for around 6 hours.

Final trimming of the film 13 and/or mesh 12 composites can be accomplished with scissors, a knife, or like device or technique.

A unique property of embodiments of the film 13 is that its hydrophilic properties and structural stiffness help it to stick to the surgical site, e.g., like Velcro™. This allows for very precise placement and also assists in retaining the mesh 12 in place with great conformation to the surgical site or anatomical structures. As a result, the mesh 12 can be "worked in" to blend with and conform to tissue.

Implementation of the methylcellulose film 13 with mesh or implant 12 embodiments constructed of unitary film constructs (e.g., FIGS. 3, 7-10), such as those disclosed in incorporated U.S. Publication No. 2011/0144417, allows for an increased freedom in designing the permanent properties of the implant, which can be quite different from the temporary properties it includes during deployment and implantation. For instance, a unitary patterned mesh or implant 12 can include supporting structures, struts or struts series, generally extending in different directions, as shown in FIGS. 7-10. Shading indicates the film 13 applied to all or a particular portion of the implant 12. As such, each series of struts 15 or cell configurations for the implant 12 adapted to provide the necessary organ or tissue support can include the film 13 layer or coating. As such, the film 13 encapsulation can provide the requisite support to repair prolapse or other disorders, yet the overall implant 12 can still have a much improved flexibility in the one or more tensioning directions to prevent discomfort, such as dispareunia during intercourse.

Figure 8:
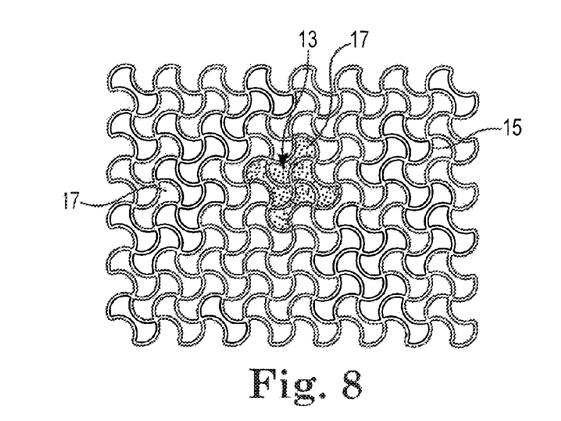
FIGS. 8-10 depict portions of a mesh or implant at least partially encapsulated or provided with a film or coating in accordance with embodiments of the present invention.
Figure 9:
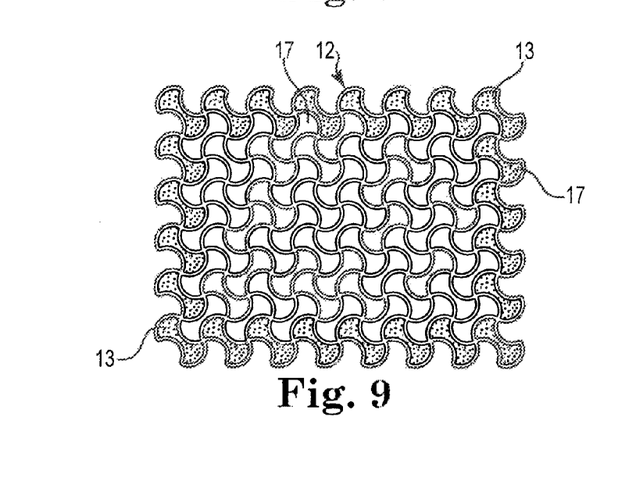
Figure 10:
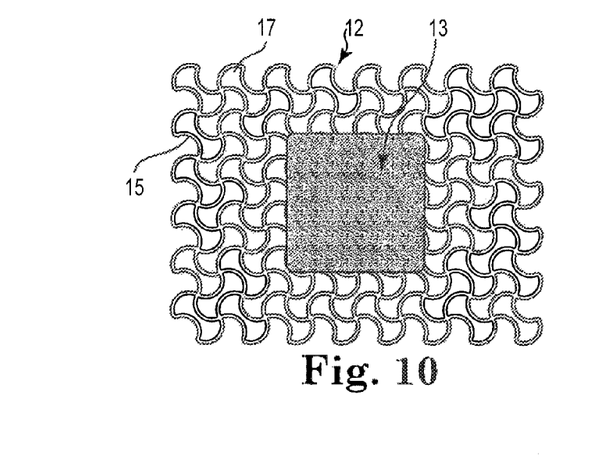

In other embodiments, select or targeted portions, such as specific or limited cells, struts 15, openings 17 can be provided with the film 13, while other portions can remain free of the film 13, as shown in FIGS. 8-9. The methylcellulose liquid-gel is very easily manipulated with syringes and can be applied to implant features with dimensions on the order of magnitude of a couple of millimeters. As a result, the gel or film 13 can be easily applied to only those select regions or structures of the implant 12 where the properties of the film 13 are considered beneficial—e.g., tissue support portions, edges, lines or regions of increased pressure or tension, and the like. Further, certain embodiments can include a mesh implant 12 with the central support portion absent any conventional mesh elements, and instead including a layer of the film 13 (FIG. 10).

Moreover, control over the areas of the implant 12 where the coating 13 is applied can be beneficial when including active drugs, substances or agents with the film 13. Namely, kinetic drug-release (KDR) is an important property when dealing with drug-eluting implants 12. By isolating the film coating 13 to specific targeted locations in well-controlled doses, the KDR can be easily manipulated to achieve optimum healing of the injured tissue, and reduce scarring. As mentioned previously, methylcellulose offers an ideal platform for short-term drug or biologics elution. Pharmaceuticals to control pain or infection, to reduce or modulate the inflammatory response, or aid in the healing process are envisioned for use with these embodiments. In certain embodiments, the time for full dissolution of the film 13 into the surrounding liquid or tissue can be approximately 20 minutes. Other time variations are envisioned, depending on various factors, such as the thickness of the film, the amount of moisture and tissue contact, the type of substance, agent or drug provided with the film 13, and the like.

Figure 11:
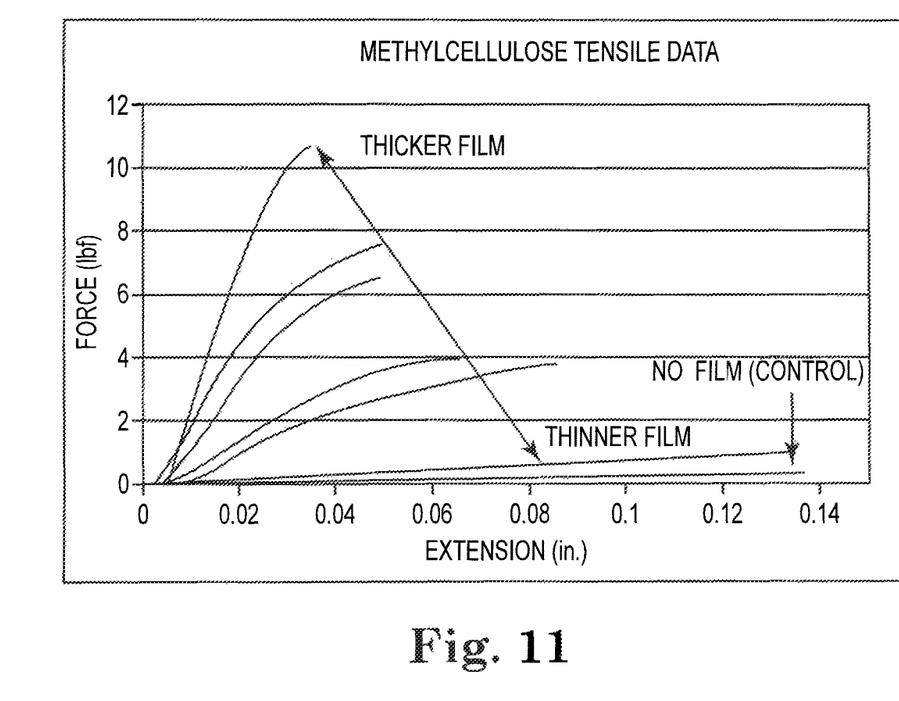
FIG. 11 is a graphical illustration of a range of values that can be achieved with the addition of a film or coating to a mesh or implant in accordance with embodiments of the present invention.

As shown in FIG. 11, the stiffness of the film encapsulated mesh 12 can increase as the thickness of the film 13 increases. This graphical illustration shows the wide range of values that can be achieved with the addition of very little film 13 material.

For those implant 12 procedures using a sheath or sleeve to facilitate implantation, such as those disclosed in the references incorporated herein, a methylcellulose film 13 can also be used to reduce the steps and the complexity of an implantation procedure for treat pelvic disorders. A polymer sheath or sleeve that holds the mesh 12 can be removed from the procedure. Instead of using the sheath, the sling or implant 12 encapsulated in film 13 itself can reduce the opportunities for the implant 12 to bunch up or curl, and to make it easier to traverse tissue during deployment without otherwise catching or snagging tissue. Tissue erosion at the treatment tissue site can also be avoided as the protective film 13 and not the implant 12 polymer material is contacting the tissue, at least during the initial stages prior to absorption of the film 13.

As referenced herein, a discrete coating of the film 13 on targeted or localized segments or areas of the mesh 12 can be accomplished with minimal processing effort. As shown in FIGS. 12-16, the localized coatings 13 can be applied to very discrete locations as well as along an entire surface of the mesh 12. For instance, discrete or localized application of the film 13 to the implant 12 can provide advantageous areas to promote tissue in-growth and healing of the tissue surrounding the implant. As described, the presence of the film 13 can create a temporary barrier of hydrogel immediately after implantation. By varying the thickness of the film 13, the hydrogel can be manipulated to absorb into the body at the optimum time in the healing process. By varying the location of the film 13 and/or the mesh 12, the tissue in-growth and scarring can be better controlled to achieve the final desired mechanical properties of the implant 12 and the surrounding tissue. This, in turn, can provide healing control to promote a reduction in dispareunia as well as a reduction in bunching, extrusion, and erosion.

In certain embodiments, it may be desirable to have immediate in-growth take place after implantation, rather than waiting for the absorption period of the hydrogel at the porous cells or openings in the mesh. As such, a methylcellulose coating 13 could be applied to the filaments, struts or other member constructs of the implant 12, while leaving the porous cells or openings in the mesh 12 free of film 13. Therefore, the pores remain open to allow for immediate tissue in-growth.

Although various biodegradable and biocompatible polymers exist for coatings and implants, certain film 13 materials can be composed of natural polymers that have varying degradation rates through absorption or enzymatic degradation in the body. Additionally, these polymers can provide a foundation for cells to adhere to, or grow on, in order to better incorporate the implant 12 at the treatment site and to reduce the inflammatory response of the implant 12. Accordingly, increased tissue adhesion is promoted with the film 13 and implant 12 once in place, and in certain embodiments, can even eliminate the need for suturing or anchoring devices to maintain the implant 12 in place upon implantation. Table 2 provides exemplary polymers that can be used to construct, in whole or in part, the degradable, biocompatible films 13 of the present invention.

TABLE 2

| | |
|---|---|
| Maltodextrin | Ethyl Cellulose |
| Glycogen | Hydroxypropyl Cellulose |
| Hydroxyethylcellulose | Sodium Carboxymethylcellulose |
| Cellulose Acetate | (Hydroxypropyl)methyl cellulose |
| Cellulose Propionate | Hyaluronic Acid |
| Chitosan | Alginate |
| Chitin | Laminarin |
| Xylan | Mannan |
| Starch | Pectin |

The polymers used to create these films 13 may be used as received from standard sources, or chemically modified to incorporate other functionalities. Chemical modifications can include the addition of ionic groups, crosslinkable groups and photo-curable groups. These groups may be added to delay the time of film degradation or to better adhere the coating 13 to the local tissue around the implant 12. Examples of crosslinkable functional groups that may be covalently attached to polymers for implantable films 13 are provided in Table 3.

TABLE 3

| | |
|---|---|
| Acrylates | Amines |
| Methacrylates | Carboxylic Acids |
| Hydrazides | Thiocarboxylic Acid |
| Aldehydes | Cyanates |
| Thiols | Cyanoacrylates |
| Halogens | Alcohols |
| Carboxylates | Esters |
| Thioesters | Imines |
| Azides | Disulfides |
| Phosphates | Boronates |

In various embodiments, the film 13 will adhere to the tissue around the implant 12 for temporary fixation until tissue ingrowth occurs. This type of adhesion can be very slight so that the implant 12 may be moved several times. A more permanent adhesion is possible as well, with the film 13 including a nature polymer from the above list (Table 3) with at least one crosslinkable group. The crosslinking groups may react directly with the tissue or may be crosslinked with an external source, such as UV light.

Figures 12, 13, 14, 14A, 15, 16:
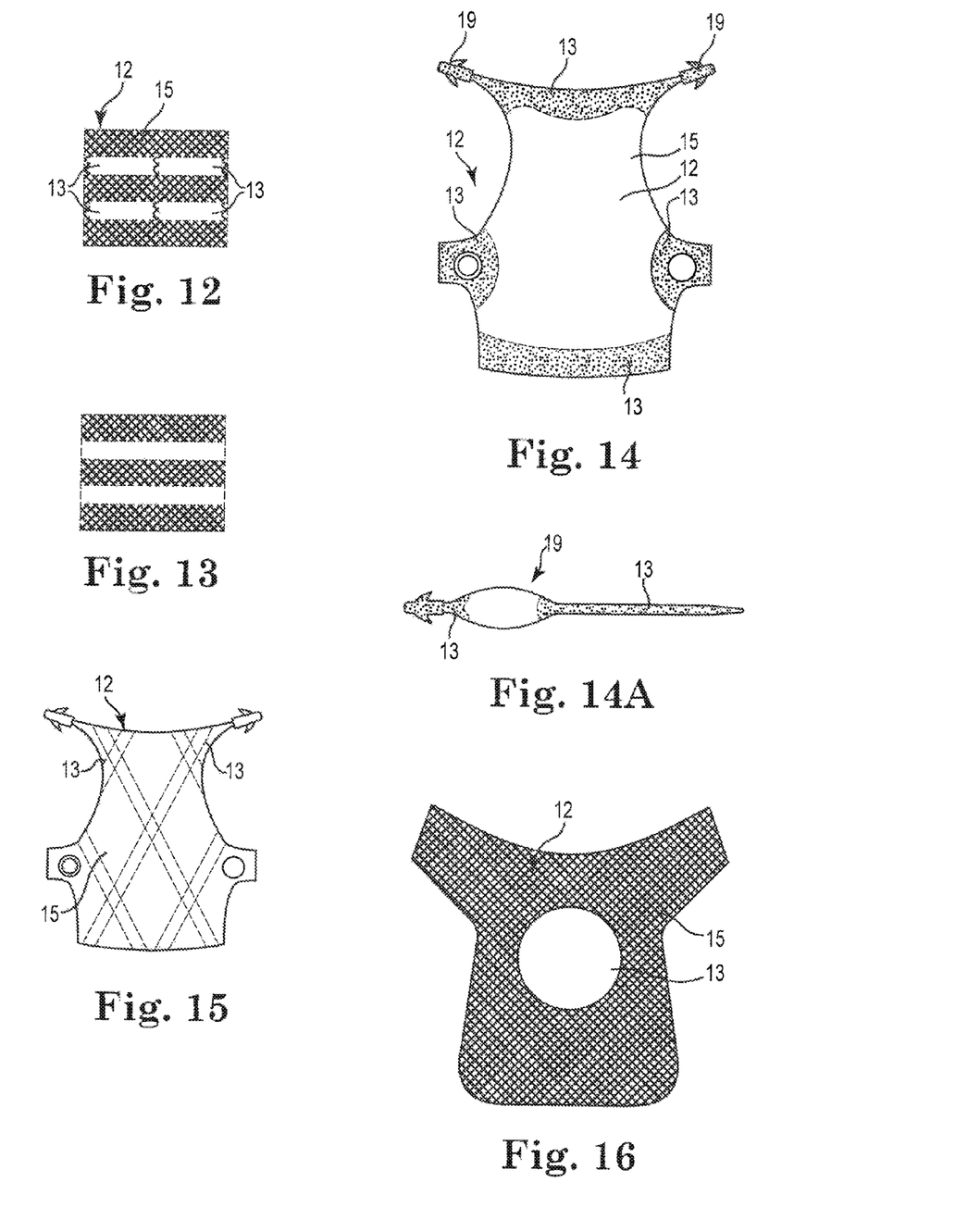
FIGS. 12-16 depict portions of a mesh or implant at least partially encapsulated or provided with a film or coating in accordance with embodiments of the present invention.

In yet other embodiments of the implant 12, portions of the implant itself can be configured to dissolve under certain circumstances. For instance, portions of the mesh implant 12 can be constructed of a material such as vicryl, PDS, monocryl, or the like. Exemplary configurations of the implant 12 having designated areas or regions with the coating 13 adapted to selectively dissolve or absorb are shown in FIGS. 14-15. The implant 12 and coating 13 can remain in a generally permanent and stable non-absorbable state upon implantation, until exposed to a catalyst. The catalyst essentially permits the physician or surgeon to "flip a switch" if needed in order to change a permanent material to a non-permanent material. Exposure of the film or coating 13 to enzymes, cryo, pH, radiation, greenlight laser frequencies, RF, microwaves, temperature extremes and the like can be employed to provide the necessary catalyst to provide the desired dissolution of the implant 12, or that coated portion of the implant 12. This can be extremely useful for patients suffering or complaining of pelvic pain after the implantation procedure has occurred. The physician can bring the patient in, apply the catalyst (e.g., transvaginal injection of an "Enzyme A" to the coating 13), with the implant 12 thereby breaking down to alleviate the patient's discomfort.

Figure 17:
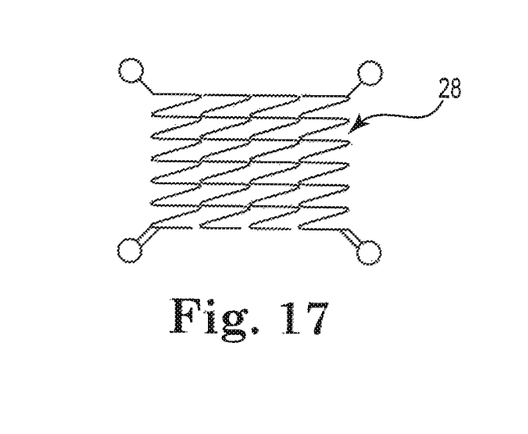
FIGS. 17-19 depict a method of forming a mesh or implant from a film material using a lithography technique in accordance with embodiments of the present invention.
Figure 18:
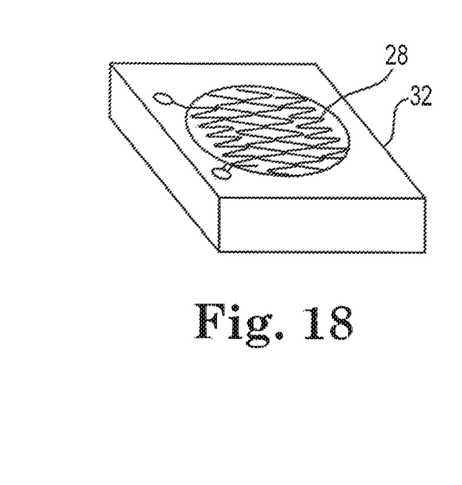
Figure 19:
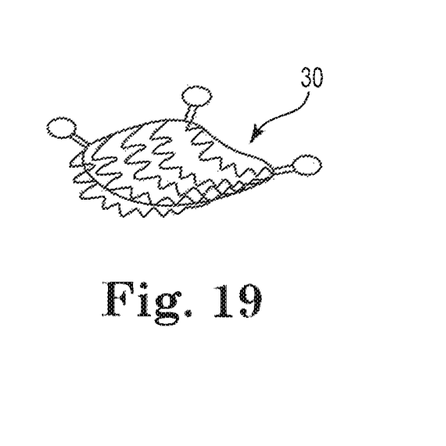

Referring generally to FIGS. 17-19, a method and process of forming a mesh or implant 30 from a film material is disclosed. For instance, a lithography technique can be employed to form all or a part of the implant 30. In certain embodiments, a light sensitive (photoresist) polyimide can be used. Other like materials can be employed as well to achieve the desired mesh construct as described and depicted herein.

In one method of formation, a liquid light sensitive polyimide is spun on a wafer substrate and baked to create a uniform film 28 of a desired thickness and structure. Next, the film 28 is exposed through a mask to transfer a lattice design to the film 28. The film 28 can be developed and rinsed to create the lattice structure. The lattice is released from the flat substrate and placed in a 3D molding surface 32 (mold may have 2 sides to enclose the lattice film 28 and hold it in the desired shape). The film 28 can then be cured at a high temperature (e.g., 300 Celsius to 350 Celsius) to complete polymer crosslinking and lock the lattice into the final 3D shape for the implant 30.

Accordingly, customizable lattices for a wide variety of design options is provided and the 3D implant can be formed to closely fit or match with specific and often complicated anatomical structures. Further, the method is repeatable at a relatively low cost.

The implant systems, their various components, structures, features, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well. Further, the system and its components or structures can be constructed of known and compatible materials know to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An implant device for treating a pelvic condition, comprising: a mesh implant device having, a plurality of members defining a plurality of openings, the mesh implant device adapted to support pelvic tissue of a patient; and a methylcellulose film coupled to the plurality of members, the methylcellulose film including a flexible polymer coating before the mesh implant is implanted into a body of the patient, the methylcellulose having a first stiffness before the mesh implant is implanted into the body of the patient, the methylcellulose film configured to absorb moisture after the mesh implant is implanted into the body of the patient, the methylcellulose film configured to have a hydrogel in response to the methylcellulose film absorbing moisture, the methylcellulose film configured to have a second stiffness in response to the methylcellulose film absorbing moisture, the second stiffness being less than the first stiffness.

2. The implant device of claim 1, wherein the mesh implant device is constructed at least in part of a polypropylene material.

3. The implant device of claim 1, further including one or more tissue anchoring devices.

4. The implant device of claim 1, wherein the methylcellulose film includes a hydrophilic polymer.

5. The implant device of claim 1, wherein the methylcellulose film fills in one or more of the plurality of openings of the mesh implant device.

6. The implant device of claim 1, wherein the plurality of members are a plurality of woven or knitted filament members.

7. The implant device of claim 1, wherein the plurality of members are a plurality of strut members defining a unitary mesh implant device.

8. The implant device of claim 1, wherein the methylcellulose film encapsulates a limited portion of the mesh implant device to define at least one absorbable film band for the mesh implant device.

9. The implant device of claim 1, wherein the mesh implant device is generally elongate and is adapted to support a urethra to treat incontinence.

10. The implant device of claim 1, wherein the mesh implant device is adapted to support pelvic tissue in treating vaginal prolapse.

11. The implant device of claim 1, wherein the mesh implant device is adapted to support tissue for treating fecal incontinence.

12. A method of treating a pelvic disorder in a patient, comprising:

providing a mesh implant having a support portion adapted to support pelvic tissue, the mesh implant further having a plurality of members defining a plurality of openings, the plurality of members of the mesh implant being encapsulated with a methylcellulose film to place the mesh implant within a tensioned state, the mesh implant having a first length in the tensioned state; and deploying the mesh implant having the methylcellulose film to a target site within the patient, the support portion providing support to the pelvic tissue; and absorbing moisture by the methylcellulose film and lengthening the mesh implant to a second length in response to the methylcellulose film absorbing moisture, wherein, in response to the methylcellulose film absorbing moisture, tension is removed, and the mesh implant transitions from the tensioned state to a natural state.

13. The method of claim 12, wherein the mesh implant is constructed at least in part of a polypropylene material.

14. The method of claim 12, wherein the mesh implant further includes one or more tissue anchoring devices.

15. The method of claim 12, wherein the methylcellulose film fills in one or more of the plurality of openings of the mesh implant.

16. The method of claim 12, wherein the plurality of members are a plurality of woven or knitted filament members.

17. The method of claim 12, wherein the plurality of members are a plurality of strut members defining a unitary mesh implant.

18. The method of claim 12, wherein the mesh implant is generally elongate and is adapted to support a urethra to treat incontinence.

19. The method of claim 12, wherein the mesh implant is adapted to support pelvic tissue in treating vaginal prolapse.

20. An implant device for treating a pelvic condition, comprising:

a mesh implant device having a plurality of members defining a plurality of openings, the mesh implant device adapted to support pelvic tissue of a patient; and a methylcellulose film encapsulating the plurality of members, the methylcellulose film including a translucent flexible polymer coating before the mesh implant is implanted into a body of the patient, the methylcellulose film having a first stiffness before the mesh implant is implanted into the body of the patient, the mesh implant device having a first length before the mesh implant device is implanted into the body of the patient, the methylcellulose film configured to absorb moisture after the methylcellulose film is inserted into the body of the patient, the methylcellulose film configured to have a hydrogel in response to the methylcellulose film absorbing moisture, the methylcellulose film configured to have a second stiffness in response to the methylcellulose film absorbing moisture, the second stiffness being less than the first stiffness, the mesh implant device configured to have a second length in response to the methylcellulose film absorbing moisture, the second length being greater than the first length.

* * * * *